United States Patent [19]
Akieda et al.

[11] Patent Number: 5,105,021
[45] Date of Patent: Apr. 14, 1992

[54] PREPARATION OF A DIFLUOROHALOMETHOXYBENZENE

[75] Inventors: Hideyuki Akieda; Naoki Sato; Koichi Morinaga; Yoshinori Ide; Ryuichi Mita; Mitsumasa Umemoto, all of Omuta, Japan

[73] Assignee: Mitsui Toatsu Chemicals, Incorporated, Tokyo, Japan

[21] Appl. No.: 507,826

[22] Filed: Apr. 12, 1990

[30] Foreign Application Priority Data

Apr. 18, 1989 [JP] Japan ............................ 1-096345
May 2, 1989 [JP] Japan ............................ 1-111984
Nov. 27, 1989 [JP] Japan ............................ 1-304685

[51] Int. Cl.$^5$ .................. C07C 41/22; C07C 319/20; C07C 45/61; C07C 209/68
[52] U.S. Cl. ........................................ 568/655; 568/33; 568/51; 568/55; 568/306; 568/337; 568/442; 568/587; 568/588; 568/637; 568/643; 568/649; 558/413; 558/415; 558/416; 558/419; 558/423; 558/424; 560/11; 560/12; 560/13; 560/18; 560/21; 560/22; 560/23; 560/42

[58] Field of Search ............... 568/637, 636, 33, 51, 568/55, 655, 643, 649, 306, 337, 442, 587, 588; 558/413, 415, 416, 419, 423, 424; 560/11, 12, 13, 18, 21, 22, 23, 42, 53, 59, 65; 562/430, 434, 432, 435, 437, 438, 453, 463, 469, 474; 564/153, 154, 155, 162, 163, 169, 166, 183, 307, 440–442

[56] References Cited

U.S. PATENT DOCUMENTS 4,377,711 3/1983 Rico et al. .......................... 568/637
4,705,866 11/1987 Gastinger .......................... 548/549
4,782,094 11/1988 Numata et al. ..................... 568/637

FOREIGN PATENT DOCUMENTS 0165574 12/1985 European Pat. Off. .
63-45233 2/1988 Japan .
2189240 10/1987 United Kingdom .
2189483 10/1987 United Kingdom .

Primary Examiner—Marianne Cintins
Assistant Examiner—Margaret Argo
Attorney, Agent, or Firm—Millen, White & Zelano

[57] ABSTRACT

A higher yield of the difluorohalomethoxybenzene produced by the reaction of a metal phenolate with dibromodifluoromethane or bromochlorodifluoromethane can be obtained by conducting the addition of a metal alcoholate or a metal hydride as a reaction initiator to a solution or a suspension of an aprotic polar solvent containing the metal phenolate and dibromodifluoromethane or bromochlorodifluoromethane.

7 Claims, No Drawings

PREPARATION OF A DIFLUOROHALOMETHOXYBENZENE

BACKGROUND OF THE INVENTION

1. Field of the Invention

The present invention relates to a process for the preparation of a difluorohalomethoxybenzene.

2. Prior Art of the Invention

Difluorohalomethoxybenzene derivatives, e.g., those having the formula (I) below, are generally used for compounds having herbicidal activity or pharmacological activity and intermediates for the preparation of compounds having these activities. These derivatives can also be utilized as important intermediates in organic synthesis and are hence very valuable compounds in industry.

Particularly, 3-phenoxybenzyl 2-(4-bromodifluoromethoxyphenyl)-2-methylpropyl ether or 1-(3-phenoxyphenyl)-4-(4-bromodifluoromethoxyphenyl)-4-methylpentane, viz., compounds of Formula (III) wherein Z is Br, Y is H and A is an oxygen atom (VII) or a methylene group (VIII), respectively, are known to have a high insecticidal and acaricidal action (Japanese Patent Laid-Open Publication No. SHO 63-45233 (1988).

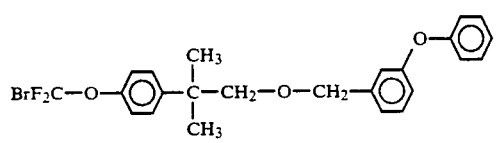

(VII)

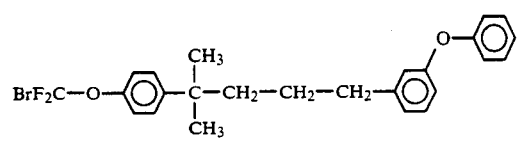

(VIII)

It is conventionally known that the difluorohalomethoxybenzene derivatives having the formula (I) below can be prepared from the reaction of a metal phenolate having the formula (II) below with dibromodifluoromethane or bromochlorodifluoromethane.

The bromodifluoromethoxylation of phenol or substituted phenols is disclosed in the following references:

1) Japanese Patent Laid-Open Publication No. SHO 58-128334 (1983) has examples for the bromodifluoromethoxylation of the substituted phenols.

According to this reference, 1 mole of sodium salt of p-hydroxybenzo-nitrile and 1.7 moles of dibromodifluoromethane are dissolved in dimethylformamide, stirred at the room temperature for a day and distilled to obtain desired p-(bromodifluoromethoxy)-benzonitrile. However, the yield is only about 31.8%.

2) Japanese Patent Laid-Open Publication No. SHO 57-109737 (1982) discloses examples for bromodifluoromethoxylation of the substituted phenols.

According to the process, 0.1 mole of potassium salt of p-cresol is dissolved in dimethylformamide, a catalytic amount of propanethiol is added, dibromodifluoromethane is further added, and reacted at 20° to 30° C. for 4 hours to obtain p-(bromodifluoromethoxy) toluene in a 21% yield.

3) According to the Journal of Fluorine Chemistry, 20, 765 (1982), o-allylphenol is dissolved in dimethylformamide, an equimolar amount of potassium hydroxide and a catalytic amount of 18-crownether-6 are added and then 2 moles of dibromodifluoromethane per mole of o-allylphenol is added. The mixture is reacted to obtain the corresponding o-(bromodifluoromethoxy)allylbenzene in a 9% yield.

4) In Tetrahedron, 37, 4209(1981), the reaction of various substituted phenols with dibromodifluoromethane are described. For example, the potassium salt of phenol is dissolved in dimethylformamide, a catalytic amount of propanethiol is added and then twice by weight of dibromodifluoromethane per weight of the potassium salt of phenol is added. The mixture is reacted to obtain the corresponding bromodifluoromethoxybenzene in a 9% yield.

Examples of the same procedures using 4-methoxyphenol, p-cresol, 4 chlorophenol and 4-nitrophenol are also described, 4-(bromodifluoromethoxy)anisole, 4-(bromodifluoromethoxy)toluene, 4-(bromodifluoromethoxy)chlorobenzene, and 4-(bromodifluoromethoxy)-nitrobenzene are obtained in the yield of 1.5%, 4%, 16% and 25%, respectively.

5) In Tetrahedron Letters, 22, 328(1981), potassium salt of phenol is dissolved in dimethylformamide, twice by mole of dibromodifluoromethane per mole of the potassium salt of phenol is added, and the mixture is reacted to obtain corresponding bromodifluoromethoxybenzene in about 9% yield.

A process for the preparation of the compounds having the above formula (VII) and formula (VIII) is also disclosed in Japanese Patent Laid-Open Publication No. SHO 63-45233(1983). 1-(3-Phenoxyphenyl)-4-(hydroxyphenyl)-4-methylpentane or 3-phenoxybenzyl 2-(4-hydroxyphenyl)-2-methylpropyl ether is dissolved in N,N'-dimethylimidazolidinone in combination with a 2 mole ratio of potassium tert-butoxide. The thus obtained solution is added dropwise at 60° C. to a solution containing 5 mole ratio of dibromodifluoromethane in N,N'-dimethylimidazolidinone. The resulting mixture is further reacted for 3 hours at the same temperature. The desired bromodifluoromethoxy compound is isolated by column chromatography. However, the yields are only about 46%.

As mentioned above, the known processes for reacting phenol or substituted phenols with dibromodifluoromethane to obtain the corresponding bromodifluoromethyl ethers provide only a low yield of the desired product.

OBJECTS OF THE INVENTION

An object of the present invention is to provide a process for the preparation of difluorohalomethoxybenzenes having herbicidal activity or pharmacological activity or which are useful as an intermediate in the synthesis of compounds having such activity.

Another object of the present invention is to provide a process for the preparation of a difluorohalomethoxybenzene of formula (VII) and formula (VIII), which compounds have high insecticidal and acaricidal action in particular.

In consideration of the present technical circumstances on the above halodifluoromethoxylation reaction of phenols, the present inventors have carried out an intensive investigation on the process of preparing a difluorohalomethoxybenzene having the formula (I) or (III) in a high yield by reacting a metal phenolate having the formula (II) or (IV), with dibromodifluoromethane or bromochlorodifluoromethane.

SUMMARY OF THE INVENTION

According to this invention, a difluorohalomethoxybenzene wherein halo is a chlorine or bromine atom is produced in high yield by reacting an alkali metal or an alkali earth metal phenolate with dibromofluoromethane or bromochlorodifluoromethane in the presence of a metal alcoholate or metal hydride.

In the preferred embodiment, the difluorohalomethoxybenzene is a compound of formula (I):

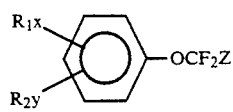

wherein $R_1$ and $R_2$ each are a hydrogen atom, lower alkyl, substituted alkyl, lower alkoxy, allyl, phenyl, phenoxy, lower alkylthio, lower alkylsulfonyl, hydroxycarbonyl, alkyloxycarbonyl, alkylaminocarbonyl, alkylcarbonyl, formyl, cyano, nitro, an amino or a halogen atom, and $R_1$ and $R_2$ may be the same or different; each of x and y is an integer of from 0 to 5, respectively, and the sum of x and y is from 1 to 5; and z is a chlorine atom or a bromine atom.

More particularly, this preferred embodiment of the invention relates to an improved process for the preparation of a difluorohalomethoxybenzene, e.g., of the above formula (I) by reacting a corresponding metal phenolate, e.g., of the formula (II):

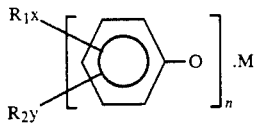

wherein $R_1$, $R_2$, x and y are the same as above, M is an alkali metal or an alkali earth metal, n is an integer of 1 or 2 wherein n is 1 when M is the alkali metal and n is 2 when M is the alkali earth metal, with dibromodifluoromethane or bromochlorodifluoromethane.

In a preferred embodiment, the invention relates to a process for the preparation of a difluorohalomethoxybenzene having the formula (III):

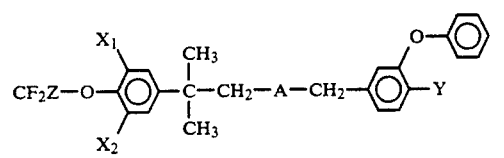

wherein each of $X_1$, and $X_2$ is independently a hydrogen atom, halogen atom or a lower alkyl, Y is a hydrogen atom or a halogen atom, Z is a chlorine atom or a bromine atom, and A is an oxygen atom or a methylene, by reaction of the corresponding metal phenolate (IV):

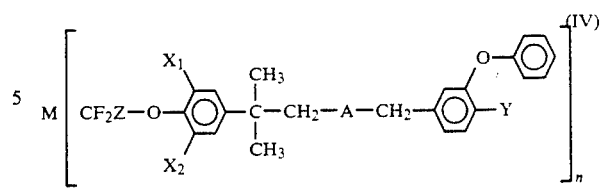

wherein $X_1$, $X_2$, Y and Z are the same as above, M is an alkali metal or an alkali earth metal, n is an integer of 1 or 2 wherein n is 1 when M is the alkali metal and n is 2 when M is the alkali earth metal, with dibromodifluoromethane or bromochlorodifluoromethane.

DETAILED DESCRIPTION OF THE INVENTION

The following phenomena have been observed.

1) It is difficult to complete the reaction merely by mixing a metal phenolate and dibromodifluoromethane in dimethylformamide as described in Japanese Patent Laid-Open Publication No. SHO 58-128334 (1983).

2) A reaction comprising the steps of dissolving a potassium salt of a substituted phenol in dimethylformamide, adding propanethiol as a catalyst and further adding dibromodifluoromethane as described in Japanese Laid-Open Patent No. SHO 57-109737 (1982), progresses under high acidity of the thiol proton. Consequently, a proton-potassium ion exchange reaction takes place between the potassium salt of the substituted phenols and propanethiol. Thus, substituted phenols remain unreacted and additionally by-products such as bromodifluorothiomethoxypropyl ether are produced.

3) In a method for preparing a metal salt of phenols by use of alcoholate such as potassium tert-butoxide as disclosed in Japanese Patent Laid-Open Publication No. SHO 63-45233 (1988):

(a) An equimolar amount of tert-butylalcohol exists in the reaction system. The tert-alcohol inhibits the desired reaction and additionally leads to generation of by-products such as difluoromethoxy compounds.

(b) The reaction is difficult to complete at relatively low temperatures by merely mixing the isolated potassium salt of 1-(3-phenoxyphenyl)-4-(4-hydroxyphenyl)-4-methylpentane or 3-phenoxybenzyl 2-(4-hydroxyphenyl)-2-methylpropyl ether with dibromodifluoromethane in N,N'-dimethylimidazolidinone.

The present inventors have found, based on the above phenomena, that the reaction of a metal phenolate having the formula (II) or the alkali metal salt of a phenol derivative having the formula (V) or formula (VI) with dibromodifluoromethane can progress very smoothly by adding a small amount of potassium tert-butoxide to a solution containing these raw materials and that the yield of the desired bromodifluoromethoxybenzene is thereby surprisingly enhanced. Thus the present invention was made on this basis.

Thus, a preferred aspect of the present invention is a process for the preparation of a difluorohalomethoxybenzene of formula (I) by reacting a metal phenolate having the formula (II) with dibromodifluoromethane or bromochlorodifluoromethane, comprising conducting the reaction of the metal phenolate having the formula (II) with dibromodifluoromethane or bromochlorodifluoromethane by the addition of a metal alcoholate or a metal hydride as a reaction initiator to a solution or a suspension in an aprotic polar solvent of the metal phenolate and dibromodifluoromethane or bromochlorodifluoromethane.

In another preferred aspect, the present invention is a process for the preparation a 3-phenoxybenzyl 2-(4-bromodifluoromethoxyphenyl)-2-methylpropyl ether (VII) or a
1-(3-phenoxyphenyl)-4-(4-bromodifluoromethoxyphenyl)-4-methylpentane (VIII) from, respectively, an alkali metal salt of a phenol derivative, having the formula (V) or the formula (VI):

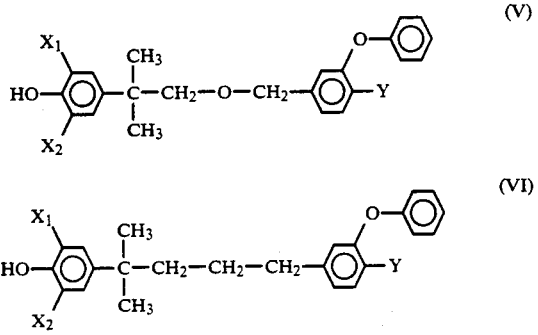

wherein $X_1$, $X_2$ and Y is the same as in the formula (III), for example, the potassium salt of 3-phenoxybenzyl 2-(4-hydroxyphenyl)-2-methylpropyl ether or 1-(3-phenoxyphenyl)-4-(4-hydroxyphenyl)-4-methylpentane, as starting material and by conducting the same reaction procedures as mentioned above.

The embodiments of the present invention will be illustrated hereinafter.

A metal phenolate, e.g., having the formula (II), i.e., an alkali metal salt or an alkali earth metal salt of a phenol compound, and dibromodifluoromethane or bromochlorodifluoromethane are used for the starting materials for the process of the present invention.

The phenol compound is not limited to the illustrated compounds and practically can be phenol or any ring substituted phenol. Examples of ring substituted phenols are monosubstituted phenols such as o-cresol, m-cresol, p-cresol, 2-ethylphenol, 3-ethylphenol, 4-ethylphenol, 2-n-propylphenol, 3-n-propylphenol, 4-n-propylphenol, 2-isopropylphenol, 3-isopropylphenol, 4-isopropylphenol, 2-phenoxyphenol, 3-phenoxyphenol, 4-phenoxyphenol, 2-nitrophenol, 3-nitrophenol, 4-nitrophenol, 2-methoxyphenol, 3-methoxyphenol, 4-methoxyphenol, 2-ethoxyphenol, 3-ethoxyphenol, 4-ethoxyphenol, 2-methylsulfonylphenol, 3-methylsulfonylphenol, 4-methylsulfonylphenol, 2-chlorophenol, 3-chlorophenol, 4-chlorophenol, 2-bromophenol, 3-bromophenol, 4-bromophenol, 2-fluorophenol, 3-fluorophenol, 4-fluorophenol, methyl or ethyl 2-hydroxybenzoate, methyl or ethyl 3-hydroxybenzoate, methyl or ethyl 4-hydroxybenzoate, 2-methylthiophenol, 3-methylthiophenol, 4-methylthiophenol, 2-ethylthiophenol, 3-ethylthiophenol, 4-ethylthiophenol, 2-allylphenol, 3-allylphenol, 4-allylphenol, 2-hydroxybenzonitrile, 3-hydroxybenzonitrile, 4-hydroxybenzonitrile, 2-phenylphenol, 3-phenylphenol, 4-phenylphenol, 2-acetylphenol, 3-acetylphenol, 4-acetylphenol, 2-hydroxybenzoic acid, 3-hydroxybenzoic acid, 4-hydroxybenzoic acid, 2-hydroxybenzoic acid diethylamide, 3-hydroxybenzoic acid diethylamide, 4-hydroxybenzoic acid diethylamide, 2-acetoaminophenol, 3-acetoaminophenol, 4-acetoaminophenol, 2-formylphenol, 3-formylphenol, 4-formylphenol, 2-diethylaminophenol, 3-diethylaminophenol, 4-diethylaminophenol, 2-dimethylaminophenol, 3-dimethylaminophenol and 4-dimethylaminophenol; disubstituted phenols such as 2,3-xylenol, 2,4-xylenol, 2,6-xylenol, 2,4-dinitrophenol, 2,6-dinitrophenol, 2,6-dimethoxyphenol, 3,5-dimethoxyphenol, 2,3-dichlorophenol, 2,4-dichlorophenol, 2,5-dichlorophenol, 2,6-dichlorophenol, 3,4-dichlorophenol, 3,5-dichlorophenol, 2-chloro-4-trifluoromethylphenol, 2-chloro-4-nitrophenol, 2-chloro-6-nitrophenol, 4-chloro-2-nitrophenol, 2-phenoxy-4-methylphenol, 3-methoxy-5-methylphenol, 2-methoxy-4-methylphenol, 4-chloro-m-cresol, 4-chloro-o-cresol, 6-chloro-m-cresol and 6-chloro-o-cresol; trisubstituted phenols such as 2,4,6-trichlorophenol, 2,4,5-trichlorophenol, 2,3,5-trimethylphenol, 2,3,6-trimethylphenol, 2,4,6-trimethylphenol, 2,6-dichloro-4-trifluoromethylphenol, 2,4-dichloro-6-methylphenol and 2,6-dichloro-4-nitrophenol; and also tetra- and penta-substituted phenols.

As to the phenol compound used as starting material, phenol derivatives having a more complex structure e.g., those represented by the formula (V) or formula (VI) can also be used for the starting material in addition to the above substituted phenols having a relatively simple structure.

The complex phenol compound used for the raw material includes, for example, 3-phenoxybenzyl 2-(4-hydroxyphenyl)-2-methylpropyl ether,
3-phenoxy-4-fluorobenzyl 2-(4-hydroxyphenyl)-2-methylpropyl ether,
3-phenoxy-4-fluorobenzyl 2-(3-chloro-4-hydroxyphenyl)-2-methylpropyl ether,
3-phenoxy-4-fluorobenzyl 2-(3-ethyl-4-hydroxyphenyl)-2-methylpropyl ether,
3-phenoxy-4-fluorobenzyl 2-(3,5-dimethyl-4-hydroxyphenyl)-2methylpropyl ether,
1-(3-phenoxyphenyl)-4-(4-hydroxyphenyl)-4-methylpentane, and 1-(3-phenoxy-4-fluorophenyl)-4-(4-hydroxyphenyl)-4-methylpentane.

Representative examples of the alkali metal atom or the alkali earth metal atom which constitute the alkali metal salt or the alkali earth metal salt of the above phenol compound include lithium, sodium, potassium, rubidium, cesium, beryllium, magnesium, calcium, strontium and barium. More preferred atoms are lithium, sodium, potassium and calcium with sodium and potassium especially preferred.

The other raw material, viz., dibromodifluoromethane or bromochlorodifluoromethane, is preferably used in an amount of one equivalent or more per equivalent of the metal phenolate having the formula (II). No particular restriction is imposed upon the upper limit of difluorodihalomethane and generally used in a mole ratio of 20 or less, more preferably in a mole ratio of 1.1 to 10 in view of economy. The excess can be removed and reused.

In the process of the present invention, the alkali metal salt or the alkali earth metal salt of the phenol compound having the formula (II) is reacted with dibromodifluoromethane or bromochlorodifluoromethane in an organic solvent. Preferred organic solvents are aprotic polar solvents.

Exemplary aprotic polar solvents suitable for use includes N,N'-dimethylformamide, dimethylsulfoxide, hexamethylphosphortriamide, N-methylpyrrolidone, N,N'-dimethylformamide dimethyl acetal, N,N'-dimethylimidazolidinone, dioxane, sulfolane and N,N'-dimethylpropyleneurea.

A single organic solvent is generally used but a mixture may also be used without any trouble.

There is no particular limitation on the amount of the solvent which is used. However, in view of volume efficiency, the solvent is usually used in an amount of 20 times by weight or less per total weight of the metal phenolate having the formula (II) and dibromodifluoromethane or bromochlorodifluoromethane. Preferred amount is 10 times by weight or less.

The process of the present invention can be achieved by dissolving or suspending the selected metal phenolate, e.g., of formula (II), and dibromodifluoromethane or bromochlorodifluoromethane in the above aprotic polar solvent, and then adding the metal alcoholate or the metal hydride directly thereto with stirring or adding dropwise the solution or suspension of the aprotic polar solvent containing the metal alcoholate or the metal hydride.

The metal alcoholate or the metal hydride which is used for the initiator of the reaction includes, for example, metal alcoholates of alcohols of 1-8 carbons atoms, preferably 1-4 carbons atoms, such as lithium methoxide, sodium methoxide, sodium ethoxide, sodium-tert-butoxide, potassium-tert-butoxide potassium methoxide, and magnesium diethoxide; and metal hydrides such as lithium hydride, sodium hydride, potassium hydride and calcium hydride. The reaction initiator may be used singly or in combination.

When the amount of the reaction initiator is too small, the object of the invention is not achieved. On the other hand, too much amount of the reaction initiator tends to induce side reactions and decrease the yield of the desired product. Hence, the amount is usually in the range of 0.01 to 2 equivalents, preferably 0.05 to 1 equivalent, per equivalent of the metal alcoholate.

In the process of the invention, the reaction temperature is not critical and is generally from 0° to 100° C., preferably from 5° to 60° C. The reaction can progress smoothly under such condition and is usually completed within 10 hours.

The end point of the reaction can be readily determined by means of thin layer chromatography or high performance liquid chromatography.

After completing the reaction, the desired product can be isolated in a conventional manner, for example by the following procedures. The reaction mixture is poured into water, neutralized with a mineral acid such as hydrochloric acid or sulfuric acid, extracted with a water insoluble solvent such as benzene and dichloromethane, and subjected to purification treatment such as washing with water. Then the solvent is distilled off to obtain crude product. The crude product is purified by distillation or fractional crystallization and column chromatography to obtain the difluorohalomethoxybenzene. By using the process of the present invention, a difluorohalomethoxybenzene of formula (I) can be produced in a yield of 70% or more.

The present invention will hereinafter be illustrated in further detail by way of the following examples.

The analysis by high performance liquid chromatography in the examples was carried out by the following conditions. (Analytical Conditions by High Performance Liquid Chromatography)
Column:
YMC Rack A-312 (ODS)
6 mm diameter × 15 cm length
Eluate: $CH_3CN/H_2O$ 10/1 (by volume)
Flow rate: 0.4 ml/min.
Detector: UV spectrophotometer (wave length 254 nm)

EXAMPLE 1

Synthesis of bromodifluoromethoxybenzene.

To a 3000 ml four necked flask equipped with a thermometer, stirrer, dropping funnel and chilling condenser, 1347 g (6.4 moles) of dibromodifluoromethane was charged and a suspension containing 169.8 g (1.28 moles) of potassium phenolate in 1560 g of N,N'-dimethylimidazolidinone (hereinafter abbreviated as DMI) was added. Then a solution containing 50 g (0.45 mole) of commercial potassium tert-butoxide in 200 ml of DMI was added dropwise to the mixture while maintaining the temperature at 25° C. After finishing the dropwise addition, the reaction was further continued for an hour at the same temperature. After completing the reaction, the reaction mixture was poured into 1000 ml of ice water and neutralized with a 10% aqueous sulfuric acid solution. The separated organic layer was extracted three times with 500 ml of dichloromethane. The dichloromethane solution thus obtained was washed with water and dried over anhydrous sodium sulfate. Sodium sulfate was filtered and dichloromethane was distilled off under atmospheric pressure. The residue was distilled under reduced pressure to obtain 233 g of colorless oil having a boiling point of 94° C./34 mm Hg. The oil was analyzed by high performance liquid chromatography. The content of bromodifluoromethoxybenzene was 98.9%. The yield was 80.4% based on phenol.

| | Elementary analysis (%) | | | |
| --- | --- | --- | --- | --- |
| | C | H | F | Br |
| Found | 37.68 | 2.37 | 17.00 | 34.29 |
| Calculated | 37.70 | 2.25 | 17.04 | 35.33 |

$^1$H-NMR $\delta H(CDCl_3)$ 7.1~7.6 ppm(s)

EXAMPLES 2-11

The reaction in Example 1 was carried out by changing kinds of solvent, phenol compound and metal salt; kinds and amounts of reaction initiator, amount of dibromodifluoromethane gas and reaction time. Results are illustrated in Table 1.

REFERENCE EXAMPLE 1

Synthesis of potassium salt of 3-phenoxybenzyl 2-(3-chloro-4-hydroxyphenyl)-2-methylpropyl ether.

In a 500 ml four necked flask, 38.3 g (0.1 mole) of 3-phenoxybenzyl 2-(3-chloro-4-hydroxyphenyl)-2-methylpropyl ether, 5.9 g (0.1 mole) of flaked 95% potassium hydroxide and 250 ml of xylene were mixed and heat-dehydrated by refluxing for 6 hours to obtain an orange uniform solution.

Xylene was distilled off under reduced pressure from the reaction mixture to obtain potassium salt of 3-phenoxybenzyl 2-(3-chloro-4-hydroxyphenyl)-2-methylpropyl ether as a yellow solid.

In addition, the same synthetic procedures as conducted in Reference Example 1 were carried out by using sodium hydroxide or lithium hydroxide in place of potassium hydroxide. Thus, corresponding salts of 3-phenoxybenzyl 2-(3-chloro-4-hydroxyphenyl)-2-methylpropyl ether were prepared.

EXAMPLE 12

Synthesis of 3-phenoxybenzyl 2-(3-chloro-4-bromofluoro-methoxyphenyl)-2-methylpropyl ether.

To a 500 ml four necked flask equipped with a thermometer, #stirrer, dropping funnel and chilling condenser, 108 g (0.52 mole) of dibromodifluoromethane was charged and a suspension containing 42.1 g (0.1 mole) of potassium salt of 3-phenoxybenzyl 2-(3-chloro-4-hydroxyphenyl)-2-methylpropyl ether in 100 ml of N,N'-dimethylimidazolidinone (DMI) was gradually added at temperature of 20° C. or less. Then a suspension containing 3.2 g (0.13 mole) of dried 97% sodium hydride in 82.7 ml of DMI was added dropwise to the mixture while maintaining the temperature at 45° C.

After finishing the dropwise addition, the reaction was further continued for an hour at the same temperature. After completing the reaction, the reaction mixture was poured into 100 ml of ice water and adjusted pH to 5 to 6 with a 10% aqueous hydrochloric acid solution. The separated organic layer was extracted three times with 500 ml of benzene. The benzene solution thus obtained was washed with water and dried over anhydrous sodium sulfate. Sodium sulfate was filtered and benzene was distilled off under reduced pressure to obtain 49.2 g of light yellow oil.

The oil was analyzed by high performance liquid chromatography. The content of 3-phenoxybenzyl 2-(3-chloro-4-bromodifluoro-methoxy-phenyl)-2-methylpropyl ether was 73.5%.

The oil was further purified by silica gel column chromatography using a ⅓ mixture of benzene/hexane as developing solvent to obtain 35.8 g of desired 3-phenoxybenzyl 2-(3-chloro-4-bromodifluoromethoxyphenyl)-2-methylpropyl ether. The yield was 69.9% based on 3-phenoxybenzyl 2-(3-chloro-4-hydroxyphenyl)-2-methylpropyl ether.

| | Elementary analysis (%) | | | | |
|---|---|---|---|---|---|
| | C | H | F | Cl | Br |
| Found | 56.58 | 4.83 | 7.45 | 6.94 | 15.80 |
| Calculated | 56.32 | 4.33 | 7.42 | 6.93 | 15.61 |

Refractive index ($n_2^{23}$): 1.5812
IR max: 1590, 1580, 1455, 1260, 1225,
(nujol)cm$^{-1}$:1200, 1170, 1150, 1115, 1070, 1020, 780, 700
N.M.R  $\delta H(CDCl_3)$:  1.32(6H,s), 3.42(2H,s),4.45(2H,s), 5.8~7.5 (12H,m)

EXAMPLE 13 AND 14

The reaction in Example 12 was carried out by changing kinds of metal salt of 3-phenoxybenzyl 2-(3-chloro-4-hydroxyphenyl)-2-methylpropyl ether, kinds and amounts of the reaction initiator, amount of dibromofluoromethane, reaction temperature and reaction time. Results are illustrated in Table-2.

REFERENCE EXAMPLE 2

Synthesis of potassium salt of 3-phenoxybenzyl 2-(4-hydroxy phenyl)-2-methylpropyl ether.

In Reference Example 1, 34.8 g (0.1 mole) of 3-phenoxybenzyl 2-(4 hydroxyphenyl)-2-methylpropyl ether was used in place of 38.3 g of 3-phenoxybenzyl 2-(3-chloro-4-hydroxyphenyl)-2-methylpropyl ether and mixed with 5.9 g (0.1 mole) of flaked 95% potassium hydroxide and 200 ml of xylene. The mixture was heat-refluxed to obtain a uniform light yellow solution. The same post-treatment as conducted in Reference Example 1 was carried out to obtain 38.7 g of potassium salt of 3-phenoxybenzyl 2-(4-hydroxyphenyl)-2-methylpropyl ether as light yellow solid.

Additionally, calcium salt was synthesized by the same procedures as above except that calcium hydroxide was used in place of potassium hydroxide.

EXAMPLE 15

Synthesis of 3-phenoxybenzyl 2-(4-bromodifluoromethoxyphenyl)-2-methylpropyl ether.

To a 400 ml four necked flask equipped with a thermometer, stirrer, dropping funnel and chilling condenser, 108 g (0.52 mole) of dibromodifluoromethane was charged and a suspension containing 38.7 g (0.1 mole) of potassium salt of 3-phenoxybenzyl 2-(4-hydroxyphenyl)-2-methylpropyl ether in 100 ml of N,N'-dimethylimidazolidinone (DMI) was gradually added at temperature of 20° C. or less. Then a suspension containing 3.7 g (0.033 mole) of potassium tert-butoxide in 21 ml of DMI was added dropwise to the mixture while maintaining the temperature at 25° C.

After finishing the dropwise addition, the reaction was further continued for an hour at the same temperature. After completing the reaction, the reaction mixture was poured into 500 ml of ice water and adjusted pH to 5 to 6 with a 10% aqueous sulfuric acid solution. The separated organic layer was extracted three times with 500 ml of benzene. The benzene solution thus obtained was washed with water and dried over anhydrous sodium sulfate. Sodium sulfate was filtered and benzene was distilled off under reduced pressure to obtain 46.3 g of light yellow oil.

The oil was analyzed by high performance liquid chromatography. The content of 3-phenoxybenzyl 2-(4-bromodifluoromethoxyphenyl)-2-methylpropyl ether was 79.7%. The yield was 77.3% based on 3-phenoxybenzyl 2-(4-hydroxyphenyl)-2-methylpropyl ether.

The oil was further purified by silica gel column chromatography using a ⅓ mixture of benzene/hexane as a developing solvent to obtain 36.4 g of desired 3-phenoxybenzyl 2-(4-bromodifluoromethoxyphenyl)-2-methylpropyl ether. The yield was 76.3% based on 3-phenoxybenzyl 2-(4 hydroxyphenyl)-2-methylpropyl ether.

| | Elementary analysis (%) | | | |
|---|---|---|---|---|
| | C | H | F | Br |
| Found | 60.57 | 4.86 | 7.94 | 16.83 |
| Calculated | 60.39 | 4.86 | 7.96 | 16.74 |

Refractive index ($n_D^{23}$) : 1.5546
IR max : 1260, 1230, 1205, 1150, 1110
[nujol] cm$^{-1}$ : 1020
N.M.R.  $\delta H(CDCl_3)$ : 1.33(6H,s),  3.37(2H,s), 4.39(2H,s), 6.78~7.4(12H,m)

EXAMPLES 16 AND 17

The reaction in Example 15 was carried out by changing kind of metal salt of 3-phenoxybenzyl 2-(4-hydroxyphenyl)-2-methylpropyl ether, kind and amount of reaction initiator, amount of dibromodifluoromethane, reaction temperature and reaction time. Results are illustrated in Table 3.

COMPARATIVE EXAMPLE 1

Synthesis of 3-phenoxybenzyl 2-(4-bromodifloromethoxyphenyl)-2methylpropyl ether.

A solution containing 21.6 g (0.062 mole) of 3-phenoxybenzyl 2-(4-hydroxyphenyl)-2-methylpropyl ether and 13.9 g (0.12 mole) of potassium tert-butoxide in 120 ml of DMI, was added dropwise with stirring at 50° to 60° C. over 30 minutes to a solution of 80 g (0.39 mole) of dibromodifluoromethane in 50 ml of DMI. The resulting mixture was maintained at the same temperature for 3 hours, poured into water and extracted with toluene. The toluene solution was washed with dilute hydrochloric acid and then with water and dried. Toluene was distilled off under reduced pressure to obtain 29.4 g of residual oil. Residual oil was purified with column chromatography using 600 g silica gel and a 1 : 1 mixture of toluene and hexane as a developing solvent to obtain 12.4 g (0.026 mole) of desired 3-phenoxybenzyl 2-(4-bromodifluoromethoxyphenyl)-2-methylpropyl ether.

The yield was 41.9% based on 3-phenoxybenzyl 2-(4-hydroxyphenyl)-2-methylpropyl ether.

REFERENCE EXAMPLE 3

Synthesis of potassium salt of 1-(3-phenoxyphenyl)-4-(4-hydroxyphenyl)-4-methylpentane.

In a 500 ml four necked flask, 34.6 g (0.1 mole) of 1-(3-phenoxyphenyl)-4-(4-hydroxyphenyl)-4-methylpentane 5.9 g (0.1 mole) of flaked 95% potassium hydroxide and 200 ml of xylene were mixed and dehydrated by heat-refluxing for 6 hours to obtain a uniform light yellow-solution. Xylene was distilled off under reduced pressure to obtain 38.5 g of potassium salt of 1-(3-phenoxyphenyl)-4-(4-hydroxyphenyl)-4-methylpentane as light yellow solid.

Additionally, the same procedures as above were carried out by using calcium hydroxide in place of potassium hydroxide to obtain calcium salt of 1-(3-phenoxyphenyl)-4-(4-hydroxyphenyl)-4-methylpentane.

EXAMPLE 18

Synthesis of 1-(3-phenoxyphenyl)-4-(4-bromodifluoromethoxy-phenyl)-4-methylpentane.

To a 400 ml four necked flask equipped with a thermometer, stirrer, dropping funnel and chilling condenser, 108 g (0.52 mole) of dibromodifluoromethane was charged and a solution containing 38.5 g (0.1 mole) of potassium salt of 1-(3-phenoxyphenyl)-4-(4-hydroxyphenyl)-4-methylpentane in 100 ml of DMI was gradually added at temperature of 20° C. or less. Then a suspension containing 3.7 g (0.033 mole) of potassium tert-butoxide in 21 ml of DMI was added dropwise to the mixture while maintaining the temperature at 2.5° C. After finishing the dropwise addition, the reaction was further continued for an hour at the same temperature. After completing the reaction, the reaction mixture was poured into 500 ml of ice water and adjusted pH to 5 to 6 with a 10% aqueous sulfuric acid solution. The separated organic layer was extracted three times with 500 ml of benzene. The benzene solution thus obtained was washed with water and dried over anhydrous sodium sulfate, sodium sulfate was filtered and benzene was distilled off under reduced pressure to obtain 46.8 g of light yellow oil.

The oil was analyzed by high performance liquid chromatography.

The content of 1-(3-phenoxyphenyl)-4-(4-bromodifluoromethoxyphenyl)-4-methylpentane was 79.4%. The yield was 78.3% based on 1-(3-phenoxyphenyl)-4-(4-hydroxyphenyl)-4-methylpentane.

The oil was further purified by silica gel column chromatography using a ⅓ mixture of benzene/hexane as a developing solvent to obtain 37.6 g of desired 1-(3-phenoxyphenyl)-4-(4-bromodifluoromethoxyphenyl)-4-methylpentane. The yield was 77.8% based on 1-(3-phenoxyphenyl)-4-(4-hydroxyphenyl)-4-methylpentane.

|  | Elementary analysis (%) | | | |
| --- | --- | --- | --- | --- |
|  | C | H | F | Br |
| Found | 63.25 | 5.33 | 7.95 | 16.75 |
| Calculated | 63.17 | 5.30 | 7.89 | 16.81 |

Refractive index ($n_D^{23}$) : 1.5482
IR max : 1580, 1480, 1240, 1295, 1140
[nujol] cm$^{-1}$ : 1095, 1000
N.M.R. $\delta$H(CDCl$_3$) : 1.1~1.8(4H,s), 1.28(6H,s) 2.47(2H,s), 6.6~7.4(13H,m)

EXAMPLES 19 AND 20

The reaction in Example 18 was carried out by changing kind of metal salt of 1-(3-phenoxyphenyl)-4-(4-hydroxyphenyl)-4-methylpentane, kind and amount of the reaction initiator, amount of dibromodifluoromethane, reaction temperature and reaction time. Results are illustrated in Table 4.

REFERENCE EXAMPLE 4

Synthesis of potassium salt of 1-(3-phenoxy-4-fluorophenyl)-4-(4-hydroxyphenyl)-4-methylpentane.

In Reference Example 3, 36.4 g (0.1 mole) of 1-(3-phenoxy-4-fluorophenyl)-4-(4-hydroxyphenyl)-4-methylpentane was used in place of 34.6 g of 1-(3-phenoxyphenyl)-4-(4-hydroxyphenyl)-4-methylpentane and mixed with 4.1 g (0.1 mole) of 97% sodium hydroxide and 250 ml of xylene. The mixture was heat-refluxed for 6 hours to obtain a uniform light yellow solution. The same post-treatment as conducted in Reference Example 3 was carried out to obtain 38.6 g of potassium salt of 1-(3-phenoxy-4-fluorophenyl)-4-(4-hydroxyphenyl)-4-methylpentane as light yellow solid.

Additionally, lithium salt was synthesized by the same procedures as above except that lithium hydroxide monohydrate was used in place of potassium hydroxide.

EXAMPLE 21

Synthesis of 1-(3-phenoxy-4-fluorophenyl)-4-(4-bromodifluoro-methoxyphenyl)-4-methylpentane.

To a 400 ml four necked flask equipped with a thermometer, stirrer, dropping funnel and chilling condenser, 108 g (0.52 mole) of dibromodifluoromethane was charged and a solution containing 38.6 g (0.1 mole) of potassium salt of 1-(3-phenoxy-4-fluorophenyl)-4-(4-hydroxyphenyl)-4-methylpentane in 100 ml of DMI was gradually added at temperature of 20° C. or less. Then a solution containing 3.2 g (0.13 mole) of dried 97% sodium hydride in 82.7 ml of DMI was added dropwise to the mixture while maintaining the temperature at 25° C.

After finishing the dropwise addition, the reaction was further continued for an hour at the same temperature. After completing the reaction, the reaction mixture was poured into 1000 ml of ice water and adjusted pH to 5 to 6 with a 10% aqueous hydrochloric acid solution, separated organic layer was extracted three times with 500 ml of benzene. The benzene solution thus obtained was washed with water and dried over anhydrous sodium sulfate. Sodium sulfate was filtered and benzene was distilled off under reduced pressure to obtain 46.8 g of light yellow oil.

The oil was analyzed by high performance liquid chromatography. the content of 1-(3-phenoxy-4-fluorophenyl)-4-(4-bromodifluoro-methoxyphenyl)-4-methylpentane was 77.3%. The yield was 77.3% based on 1-(3-phenoxy-4-fluorophenyl)-4-(4-hydroxyphenyl)-4-methylpentane.

The oil was further purified by silica gel column chromatography using a ⅓ mixture of benzene/hexane as a developing solvent to obtain 36.9 g of desired 1-(3-phenoxy-4-fluorophenyl)-4-(4-bromodifluoromethoxyphenyl)-4-methylpentane. The yield was 77.7% based on 1-(3-phenoxy-4-fluorophenyl)-4-(4-hydroxyphenyl)-4-methylpentane.

| | Elementary analysis (%) | | | |
|---|---|---|---|---|
| | C | H | F | Br |
| Found | 60.57 | 4.86 | 7.94 | 16.80 |
| Calculated | 60.86 | 4.90 | 7.55 | 16.19 |

Refractive index ($n_D^{23}$) : 1.5480
IR max : 1580, 1050, 1485, 1280, 1210
[nujol] cm$^{-1}$ : 1160, 1140, 1000
N.M.R. $\delta H(CDCl_3)$ : 1.1~1.8(4H,m), 1.80(6H,s), 2.45(2H,s), 6.60~7.4(12H,m)

EXAMPLES 22 AND 23

The reaction in Example 21 was carried out by changing kind of metal salt of 1-(3-phenoxy-4-fluorophenyl)-4-(4-hydroxyphenyl)-4-methylpentane, kind and amount of reaction initiation, amount of dibromodifluoromethane, reaction temperature and reaction time. Results are illustrated in Table 5.

COMPARATIVE EXAMPLE 2

Synthesis of 1-(3-phenoxyphenyl)-4-(4-bromodifluoromethoxy-phenyl)-4-methylpentane.

A solution containing 20.0 g (0.58 mole) of 1-(3-phenoxyphenyl)-4-(4-hydroxyphenyl)-4-methylpentane and 13.0 g (0.11 mole) of potassium tert-butoxide in 120 ml of DMI, was added dropwise with stirring at 50° to 60° C., over 30 minutes to a solution of 80 g (0.39 mole) of dibromodifluoromethane in 50 ml of DMI. The resulting mixture was maintained at the same temperature for 3 hours, poured into water and extracted with toluene. The toluene solution was washed with dilute hydrochloric acid and then with water and dried. Toluene was distilled off under reduced pressure to obtain 29.4 g of residual oil. Residual oil was purified with column chromatography using 600 g silica gel and a 1 : 1 mixture of toluene and hexane as a developing solvent to obtain 12.6 g (0.026 mole) of desired 1-(3-phenoxyphenyl)-4-(4-bromodi-fluoromethoxyphenyl)-4-methylpentane.

The yield was 44.8% based on 1-(3-phenoxyphenyl)-4-(4-hydroxyphenyl)-4-methylpentane.

TABLE 1

| Example No. | Phenol compound (1) Substituent (2) | Phenol compound (1) Metal salt | Phenol compound (1) Solvent | CF$_2$Br$_2$ (3) (mole) | Reaction initiator (4) (mole) | Temperature (°C.)/ Time (hour) | Conversion (%) | Selectivity (%) | Yield (%) |
|---|---|---|---|---|---|---|---|---|---|
| 2 | 4-cyano | K | N,N-dimethyl-imidazolidinone | 4.5 | CH$_3$ONa (0.1) | 25/3.0 | 93.2 | 86.1 | 80.2 |
| 3 | 4-allyl | K | N,N-dimethyl-formamide | 5 | CH$_3$OK (0.1) | 10/1.3 | 92.8 | 85.1 | 79.0 |
| 4 | 4-chloro | Na | N,N-dimethyl-acetamide | 6 | (C$_2$H$_6$O)Mg (1.0) | 25/3.0 | 91.3 | 83.2 | 78.0 |
| 5 | 4-methoxy | Na | N-methyl pyrrolidone | 3 | C$_2$H$_6$ONa (0.30 | 20/2.5 | 90.3 | 82.2 | 74.2 |
| 6 | 4-methyl | Ca | hexamethyl phosphortriamide | 4 | CH$_3$ONa/CH$_3$OK (5) | 15/2.0 | 90.4 | 83.2 | 75.2 |
| 7 | 4-nitro | Ca | N,N-dimethyl-propyleneurea | 7 | NaH (0.5) | 5/5.0 | 95.9 | 85.4 | 82.9 |
| 8 | 3-phenoxy | Mg | dioxane/N,N-dimethylpropylene-urea | 5.5 | tert-C$_4$H$_9$O Na (0.07) | 20/6.0 | 81.1 | 89.2 | 72.3 |
| 9 | 4-acetyl | K | sulfolane/N,N-dimethylimidazo-lidinone (7) | 10 | CaH$_2$ (1.0) | 45/10.0 | 78.4 | 89.4 | 70.1 |
| 10 | 4-phenyl | Ca | dimethylsulfoxide | 8 | tert-C$_4$H$_9$O K (0.03) | 30/4.0 | 86.5 | 88.1 | 76.2 |
| 11 | 4-methylthio | Ba | N,N-dimethyl-formamidacetyl | 6.5 | KH (0.05) | 15/6.0 | 93.4 | 75.3 | 70.3 |
| 12 | 4-methyl sulfonyl | Na | N,N-dimethylimi-dazo-lidinone | 15 | LiH (0.8) | 40/10.0 | 78.3 | 89.2 | 69.8 |
| 13 | 2-chloro-4-methyl | K | N,N-dimethylpropyleneurea | 4 | tert-C$_4$H$_9$O K (0.1) | 25/4.0 | 83.1 | 84.2 | 70.0 |

Note:
(1) The same moles as in Example 1 were used in the reaction.
(2) Substituent is R in the formula (I).
(3) Mole ratio to the raw material phenol compound.
(4) Mole ratio to the raw material phenol compound.
(5) CH$_3$OK/CH$_3$ONa = ⅔ by mole.
(6) dioxane/N,N-dimethylpropyleneurea = 10/1 by mole.
(7) sulfolane/N,N-dimethylimidazolidinone = 10/1 by mole.

TABLE 2

| Example No. | Metal salt (1) | CF$_2$Br$_2$ (mole) | Reaction initiator Compound | Amount (mole) | Temperature (°C.)/ Time (hour) | Yield (g) | HPLC value (2) | Yield (%) |
|---|---|---|---|---|---|---|---|---|
| 13 | Li | 0.33 | tert-C$_4$H$_9$OK | 0.033 | 45/2.0 | 48.3 | 73.2 | 69.5 |
| 14 | Na | 0.85 | C$_2$H$_5$ONa | 0.88 | 10/6.0 | 48.0 | 74.8 | 70.3 |

Note:
(1) Metal salt of 3-phenoxybenzyl 2-(3-chloro-4-hydroxyphenyl)-2-methylpropyl ether (0.1 mole)
(2) HPLC value of 3-phenoxybenzyl 2-(3-chloro-4-bromodifluoromethoxyphenyl)-2-methylpropyl ether (internal standard method)

TABLE 3

| Example No. | Metal salt (1) | CF$_2$Br$_2$ (mole) | Reaction initiator Compound | Amount (mole) | Temperature (°C.)/ Time (hour) | Yield (g) | HPLC value (2) | Yield (%) |
|---|---|---|---|---|---|---|---|---|
| 16 | K | 0.33 | CH$_3$ONa | 0.08 | 40/1.0 | 46.6 | 78.3 | 76.5 |
| 17 | Ca | 0.85 | NaH | 0.13 | 15/4.0 | 45.8 | 72.3 | 69.4 |

Note:
(1) Metal salt of 3-phenoxybenzyl 2-(4-hydroxyphenyl)-2-methylpropyl ether (0.1 mole)
(2) HPLC value of 3-phenoxybenzyl 2-(4-bromodifluoromethoxyphenyl)-2-methylpropyl ether (internal standard method)

TABLE 4

| Example No. | Metal salt (1) | CF$_2$Br$_2$ (mole) | Reaction initiator Compound | Amount (mole) | Temperature (°C.)/ Time (hour) | Yield (g) | HPLC value (2) | Yield (%) |
|---|---|---|---|---|---|---|---|---|
| 19 | K | 0.33 | NaH | 0.08 | 40/1.0 | 46.2 | 79.8 | 77.6 |
| 20 | Ca | 0.85 | CH$_3$ONa | 0.13 | 15/4.0 | 45.9 | 72.8 | 70.3 |

Note:
(1) Metal salt of 1-(phenoxyphenyl)-4-(4-hydroxyphenyl)-4-methylpentane
(2) HPLC value of 1-(phenoxyphenyl)-4-(4-bromodifluoromethoxyphenyl)-4-methylpentane (internal standard method)

TABLE 5

| Example No. | Metal salt (1) | CF$_2$Br$_2$ (mole) | Reaction initiator Compound | Amount (mole) | Temperature (°C.)/ Time (hour) | Yield (g) | HPLC value (2) | Yield (%) |
|---|---|---|---|---|---|---|---|---|
| 22 | Li | 0.33 | tert-C$_4$H$_9$OK | 0.033 | 45/2.0 | 45.4 | 74.3 | 71.0 |
| 23 | K | 0.85 | C$_2$H$_6$ONa | 0.08 | 10/6.0 | 45.1 | 79.8 | 75.8 |

Note:
(1) Metal salt of 1-(3-phenoxy-4-fluorophenyl)-4-(4-hydroxyphenyl)-4-methylpentane
(2) HPLC value of 1-(3-phenoxy-4-fluorophenyl)-4-(4-bromodifluoromethoxyphenyl)-4-methylpentane (internal standard method)

What is claimed is:

1. In a process for the production of a difluorohalomethoxybenzene by the reaction of a corresponding phenolate selected from the group consisting of alkali earth phenolates and alkali metal phenolates with a bromofluoromethane selected from the group consisting of dibromodifluoromethane and bromochlorodifluoromethane, the improvement which comprises dissolving or suspending the phenolate and the bromofluoromethane in an aprotic polar solvent and then adding thereto as a reaction initiator a member of the group consisting of metal alcoholate and metal hydrides.

2. The process according to claim 1, wherein the difluorohalomethoxybenzene is a compound of the formula $$R_1x\text{-}C_6H_{(3-x-y)}(R_2y)\text{-}OCF_2Z$$

wherein R$_1$ and R$_2$ each are a hydrogen atom, lower alkyl group, substituted alkyl group, lower alkoxy group, allyl group, phenyl group, phenoxy group, lower alkylthio group, lower alkylsulfonyl group, hydroxycarbonyl group, alkyloxycarbonyl group, alkylaminocarbonyl group, alkylcarbonyl group, formyl group, cyano group, nitro group, amino group or a halogen atom; x and y each is an integer of from 0 to 5, and the sum of x and y is from 1 to 5; and Z is a chlorine atom or a bromine and the metal phenolate is a compound of the formula $$[R_1x\text{-}C_6H_{(3-x-y)}(R_2y)\text{-}O]_n \cdot M$$

wherein R$_1$, R$_2$, x and y have the values given above; M is an alkali metal or an alkali earth metal; and n is 1 when M is an alkali metal and n is 2 when M is an alkali earth metal.

3. The process according to claim 1 wherein the difluorohalomethoxybenzene is a compound of the formula

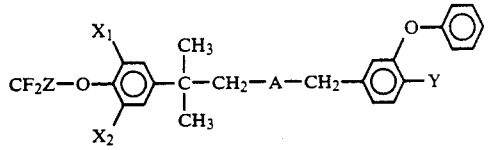

wherein each of $X_1$ and $X_2$ independently is a hydrogen atom, halogen atom or a lower alkyl group; Y is a hydrogen atom or a halogen atom; A is an oxygen atom or a methylene group; and Z is a chlorine atom or a bromine atom and the metal phenolate is an alkali metal salt or an alkali earth metal salt of a phenol of the formula

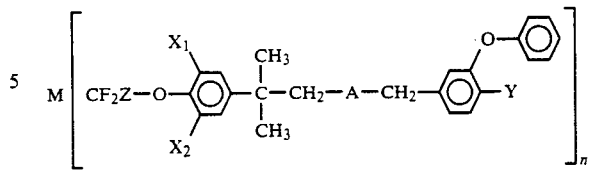

wherein $X_1$, $X_2$, Y, A and Z have the values given hereinabove. M is an alkali metal or an alkali earth metal, n is an integer of 1 or 2 wherein n is 1 when M is the alkali metal and n is 2 when M is the alkali earth metal.

4. The process of claim 1 wherein the metal alcoholate is sodium, potassium or magnesium methoxide, ethoxide or tertbutoxide and the metal hydride is sodium, potassium or calcium hydride.

5. The process of claim 1 wherein the phenolate is an alkali metal salt or alkali earth metal salt of 3-phenoxybenzyl 2-(4-hydroxyphenyl)-2-methylpropyl ether.

6. The process of claim 1 wherein the phenolate is an alkali metal salt or an alkali earth metal salt of 1-(3-phenoxyphenyl)-4-(4-hydroxyphenyl)-4-methylpentane.

7. The process of claim 1 wherein the amount of the reaction initiator employed is from 0.01 to 2 moles per mole of the metal phenolate.

* * * * *